United States Patent
Biondo et al.

(10) Patent No.: US 9,019,107 B2
(45) Date of Patent: Apr. 28, 2015

(54) METHODS AND APPARATUS FOR DETECTION AND REPORTING OF VEHICLE OPERATOR IMPAIRMENT

(71) Applicant: GM Global Technology Operations LLC, Detroit, MI (US)

(72) Inventors: William A. Biondo, Beverly Hills, MI (US); David T. Proefke, Troy, MI (US)

(73) Assignee: GM Global Technology Operations LLC, Detroit, MI (US)

( * ) Notice: Subject to any disclaimer, the term of this patent is extended or adjusted under 35 U.S.C. 154(b) by 0 days.

(21) Appl. No.: 13/922,005

(22) Filed: Jun. 19, 2013

(65) Prior Publication Data

US 2014/0375462 A1    Dec. 25, 2014

(51) Int. Cl.
*G08B 23/00* (2006.01)
*G08B 21/02* (2006.01)

(52) U.S. Cl.
CPC ...................................... *G08B 21/02* (2013.01)

(58) Field of Classification Search
CPC . B60K 28/063; B60K 28/06; B60W 2540/24; B60W 2540/28
USPC ................................ 340/425.5, 426, 506, 3.1
See application file for complete search history.

(56) References Cited

U.S. PATENT DOCUMENTS

| | | | | |
|---|---|---|---|---|
| 4,926,164 A * | 5/1990 | Porter et al. | ................... | 340/576 |
| 5,465,079 A * | 11/1995 | Bouchard et al. | .............. | 340/576 |
| 6,697,732 B1 * | 2/2004 | Gotfried | ........................ | 701/516 |
| 6,819,248 B2 * | 11/2004 | Gotfried | ..................... | 340/573.1 |
| 6,886,653 B1 * | 5/2005 | Bellehumeur | ................ | 180/272 |
| 7,173,536 B2 * | 2/2007 | Duval | ............................ | 340/576 |
| 7,256,700 B1 * | 8/2007 | Ruocco et al. | ................ | 340/576 |
| 7,823,681 B2 * | 11/2010 | Crespo et al. | .................. | 180/272 |
| 8,049,631 B1 * | 11/2011 | Edwards | ........................ | 340/576 |
| 8,196,694 B2 * | 6/2012 | Biondo et al. | ................. | 180/272 |
| 2006/0028556 A1 * | 2/2006 | Bunn et al. | ............... | 348/211.99 |
| 2009/0234677 A1 * | 9/2009 | Arezina | ............................ | 705/4 |
| 2010/0280118 A1 * | 11/2010 | Mason et al. | .................. | 514/561 |
| 2011/0304465 A1 * | 12/2011 | Boult et al. | .................... | 340/576 |

* cited by examiner

*Primary Examiner* — Daryl Pope
(74) *Attorney, Agent, or Firm* — Ingrassia Fisher & Lorenz, P.C.

(57) ABSTRACT

A method for reporting vehicle operator impairment criteria is provided. The method determines, using a substance detection device installed inside a vehicle, a level of a substance or combination of substances associated with vehicle operator impairment; obtains vehicle status data from a plurality of sensors onboard the vehicle; determines a level of risk associated with vehicle operator behavior, using the obtained vehicle status data; and generates a report, comprising the determined level of the substance or the combination of substances and the determined level of risk.

20 Claims, 3 Drawing Sheets

METHODS AND APPARATUS FOR DETECTION AND REPORTING OF VEHICLE OPERATOR IMPAIRMENT

TECHNICAL FIELD

Embodiments of the subject matter described herein relate generally to systems that report impaired behavior of persons operating vehicles or heavy machinery. More particularly, embodiments of the subject matter relate to detection and reporting of vehicle operator impairment due to substance abuse.

BACKGROUND

Operating vehicles under the influence of alcohol and other substances is a global problem. Each year, many deaths and injuries are attributable to alcohol or drug related vehicular accidents. Alcohol impairment fatalities comprise one-third of highway fatalities annually; there are over one hundred thousand fatalities globally associated with impaired driving, and there are over one million injuries globally associated with impaired driving. Impairment is the largest single factor influencing traffic fatalities. To address this problem, technologies have been developed to test for the presence and levels of alcohol and/or drugs, for the purpose of preventing a person under the influence from operating a motor vehicle.

Accordingly, it is desirable to utilize a method of reporting such driver impairment to an owner or responsible party of a vehicle, who may be unaware of his/her vehicle being operated while the driver is under the influence of alcohol or other substances. Furthermore, other desirable features and characteristics will become apparent from the subsequent detailed description and the appended claims, taken in conjunction with the accompanying drawings and the foregoing technical field and background.

BRIEF SUMMARY OF EMBODIMENTS

Some embodiments provide a method for reporting vehicle operator impairment criteria. The method determines, using a substance detection device installed inside a vehicle, a level of a substance or combination of substances associated with vehicle operator impairment; obtains vehicle status data from a plurality of sensors onboard the vehicle; determines a level of risk associated with vehicle operator behavior, using the obtained vehicle status data; and generates a report, comprising the determined level of the substance or the combination of substances and the determined level of risk.

Some embodiments provide a system for reporting impaired operation of a vehicle. The system includes a substance detection module, configured to examine a driver for presence of a substance that is likely to cause impaired driving; a risk detection module, configured to determine a risk level associated with a current operation of the vehicle by the driver; and a notification module. In some embodiments, the notification module is configured to trigger an alert notification when the substance detection module detects presence of the substance at a level exceeding an alert notification substance threshold; and the risk detection module determines a risk level exceeding an alert notification risk threshold.

Some embodiments provide a system for determining timing and priority of notification of impaired driving. The system includes a processor architecture; a memory, communicatively coupled to the processor architecture, wherein the memory is configured to store received data and instructions executable by the processor architecture; a plurality of sensors, communicatively coupled to the processor architecture, and configured to collect data associated with operation of a vehicle; and an impairing substance detection unit, communicatively coupled to the processor architecture, and configured to test for a level of an impairing substance. In some embodiments, the processor architecture is configured to determine a presence and a level of the impairing substance, using data received from the impairing substance detection unit; detect impaired driving behavior using data received from the plurality of sensors; determine a risk level based on the impaired driving behavior; and initiate a report detailing the impaired driving behavior, the risk level, and the presence of an impairing substance.

This summary is provided to introduce a selection of concepts in a simplified form that are further described below in the detailed description. This summary is not intended to identify key features or essential features of the claimed subject matter, nor is it intended to be used as an aid in determining the scope of the claimed subject matter.

BRIEF DESCRIPTION OF THE DRAWINGS

A more complete understanding of the subject matter may be derived by referring to the detailed description and claims when considered in conjunction with the following figures, wherein like reference numbers refer to similar elements throughout the figures.

DETAILED DESCRIPTION

The following detailed description is merely illustrative in nature and is not intended to limit the embodiments of the subject matter or the application and uses of such embodiments. As used herein, the word "exemplary" means "serving as an example, instance, or illustration." Any implementation described herein as exemplary is not necessarily to be construed as preferred or advantageous over other implementations. Furthermore, there is no intention to be bound by any expressed or implied theory presented in the preceding technical field, background, brief summary or the following detailed description.

The subject matter presented herein relates to methods and apparatus used to detect and report vehicle operator impairment due to alcohol and/or drug use. In certain embodiments, the system identifies a driver and vehicle type, and then detects a presence and measures a level of alcohol and/or drugs. The system then utilizes various predetermined threshold values to send a report or notification to an owner, or responsible party, of the vehicle, including data associated with driver impairment. Within the context of this application, the terms "owner" and "responsible party" may refer to any person holding some type of property right or interest over the vehicle in question, or any person in a position of responsibility or oversight over one or more vehicles. For example, a supervisor that oversees a fleet of limousines, taxi cabs, or school buses may or may not hold a direct property interest in any of the vehicles themselves, but may still be considered a responsible party for the purposes of oversight and monitoring of vehicle operator impairment and/or exhibiting risky behavior.

Figure 1:
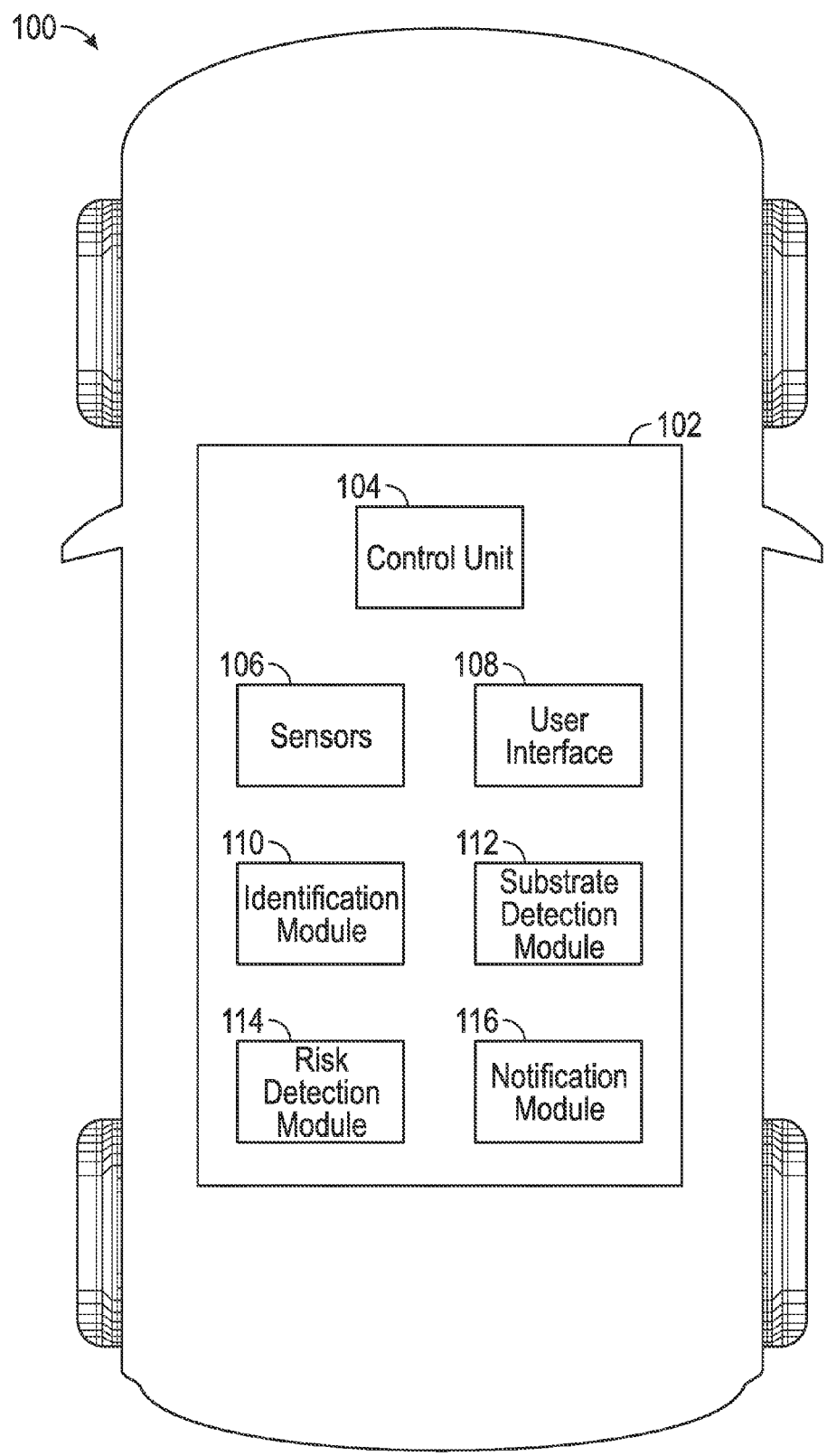
FIG. 1 is a functional block diagram of a vehicle that includes a vehicle operator impairment detection functionality, in accordance with an exemplary embodiment.

Referring now to the drawings, FIG. 1 is a functional block diagram of a vehicle 100 that includes a vehicle operator impairment detection system, in accordance with an exemplary embodiment. The vehicle 100 may be any one of a number of different types of types of automobiles (cars, trucks, motorcycles, sport-utility vehicles, vans, etc.), aviation vehicles (such as airplanes, helicopters, etc.), watercraft (boats, ships, jet skis, etc.), trains, all-terrain vehicles (snowmobiles, four-wheelers, etc.), military vehicles (Humvees, tanks, trucks, etc.), rescue vehicles (fire engines, ladder trucks, police cars, emergency medical services trucks and ambulances, etc.), spacecraft, hovercraft, and the like. Along these lines, the term vehicle operator indicates any person who assumes the majority of the responsibility for operating the vehicle at a certain time. In certain embodiments, a vehicle operator may include an airline pilot or co-pilot, a driver of an automobile, an engineer of a train, or the like.

In accordance with some embodiments, the vehicle 100 may include, without limitation: an operator impairment detection and reporting system 102; a control unit 104; a plurality of sensors 106; a user interface 108; an identification module 110; a substance detection module 112; a risk detection module 114; and a notification module 116. These elements and features of the vehicle 100 may be operatively associated with one another, coupled to one another, or otherwise configured to cooperate with one another as needed to support the desired functionality—in particular, the detection of vehicle operator impairment and reporting functionality described herein. For ease of illustration and clarity, the various physical, electrical, and logical couplings and interconnections for these elements and features are not depicted in FIG. 1. Moreover, it should be appreciated that embodiments of the vehicle 100 will include other elements, modules, and features that cooperate to support the desired functionality. For simplicity, FIG. 1 only depicts certain elements that relate to the detection of vehicle operator impairment and the drug and/or alcohol detection techniques described in more detail below.

The control unit 104 may be implemented using any application specific integrated circuit (ASIC), electronic circuit, processor (shared, dedicated, or group) and memory that execute one or more software or firmware programs, a combinational logic circuit, and/or other suitable components that provide the described functionality. In the example provided, the control unit 104 executes the tasks of the processes described herein, such as the tasks of the processes 200 and 300, described below in connection with FIGS. 2-3.

The plurality of sensors 106 located within the vehicle 100 are positioned and configured to collect data detailing vehicle operations, including speed, acceleration/deceleration, lateral acceleration/deceleration, and any "erratic" driving maneuvers, such as swerving, braking with excessive force, etc. In certain embodiments, the plurality of sensors may include, without limitation, one or more speedometers, accelerometers, brake sensors, and the like. Generally, the plurality of sensors 106 are polled by the control unit 104 and/or the risk detection module 114 to obtain collected data. However, in some embodiments, the plurality of sensors 106 may also be set to deliver data to the control unit 104 and/or the risk detection module 114 without a specific request, after particular events or at specific time intervals.

The user interface 108 includes a vehicle display and a means for providing user input. The display exhibits various menus and potential selections for a user to choose and view. In certain embodiments, the means for providing user input may also be implemented as a touch-screen on the display itself. In other embodiments, the means for providing user input may be external to the display itself, implemented as a series of buttons, knobs, sliders, or a combination of a touch-screen with external buttons, etc. The user interface 108 accepts user input to determine what is shown on a vehicle display. For example, a user might navigate through a series of menus containing categories of information for potential display. Such information may include various operating parameters, current settings, detected conditions, and the like.

The identification module 110 determines an identification of the vehicle operator and identifies a designation or type of vehicle for further analysis. In certain embodiments, the identity of the vehicle operator is a simple distinction between an owner and a non-owner of the vehicle; in other embodiments, the identity may be more specific, using a particular name for a vehicle operator. A designation, or type, of a vehicle is an owner-configurable label that may be attached to each vehicle 100, which characterizes permissible vehicle operation using specific parameters. For example, a given vehicle 100 may have any of the following vehicle types, without limitation: teen vehicle, fleet vehicle, valet vehicle, air transport vehicle, school bus vehicle, and the like.

In some embodiments, the identification module 110 is able to determine an identity of an operator of the vehicle 100 using a personalized key and/or key fob. A personalized key or key fob has been programmed for a particular driver (e.g., Driver 1, Driver 2, etc.) and enables a vehicle operator to alter certain settings of the vehicle 100 according to his/her pre-programmed preferences. The identity of a vehicle operator, as provided by the identification module 110, is also available to other systems for use in applications where a distinction between drivers is required.

Generally, the ignition key and/or key fob transmits a unique identification code to the vehicle during its normal functional requests. The vehicle then associates the unique identification code for that device with a unique driver number. This association of a unique identification code with a unique driver number is commonly used in the automatic configuration of vehicle seats, mirrors, and steering column position according to the saved preferences of a specific user. Further, it may also be used to automatically configure heating, ventilating, and air conditioning (HVAC) settings according to the saved preferences of a specific user. In addition, a specific driver type, instead of merely a specific driver, may be associated with a particular key or key fob. Since each key or key fob has a unique identification code that will be associated with a unique driver number, anytime that particular key or key fob is in use, the specified driver type would be assumed to be in operation of the vehicle. For example, a specific ignition key may be specified as belonging to a teen driver, and each time that specific ignition key is used, a teen driver is assumed to be in operation of the vehicle.

In some embodiments, the identification module 110 utilizes biometric authentication to determine an identity of an operator of the vehicle 100, which may include, without limitation, facial recognition technology, fingerprint recognition technology, retinal scan technology, voice recognition technology, or the like. In yet other embodiments, each operator of the vehicle 100 may have a unique password or alphanumeric code that must be entered before operating the vehicle 100.

The substance detection module 112 detects the presence of substances which may impair a vehicle operator. Generally, the substance detection module 112 detects the presence of alcohol and/or drugs, including both prescription drugs and illegal drugs, but may also be configured to detect any substance which may be deemed to impair the ability of a person to operate a vehicle safely. In certain embodiments, the substance detection module 112 not only detects a presence of such substances, but also measures a level or amount of the detected substance at any given time.

In some embodiments, the substance detection module 112 may be located inside and/or built into the passenger compartment of the vehicle 100. In certain embodiments, the substance detection module 112 may be factory-installed by the manufacturer of the vehicle, and in other embodiments, the substance detection module 112 may be an aftermarket device installed or otherwise placed in the vehicle after manufacture. The substance detection module 112 may be implemented, wholly or in part, utilizing tissue spectrometry, distant spectrometry, electrochemical impairment measurement, behavior impairment detection, and/or a combination of any of the previously listed technologies. In some embodiments, the substance detection module 112 detects the presence of substances actively, using for example, a breathalyzer into which a vehicle operator is required to actively exhale. In other embodiments, the substance detection module 112 detects the presence of substances passively, requiring no voluntary action on the part of the vehicle operator to obtain the necessary data, using for example, a passive breathalyzer.

The risk detection module 114 analyzes information regarding vehicle operation to determine a level of risk associated with vehicle operator behavior. The risk detection module 114 determines whether or not the vehicle operator is exhibiting high risk behavior by determining a quantity and duration of maneuvers executed by a vehicle operator, including several pre-defined "high risk" maneuvers. In certain embodiments, high risk maneuvers may include, without limitation: high g accelerations, high g decelerations, speeds above a designated threshold, lateral acceleration above a designated threshold, swerving, braking with force above a designated threshold, a maneuver which be categorized as "erratic" or "risky" driving, or any combination of the aforementioned driving maneuvers.

The plurality of sensors 106 provide data regarding vehicle operations, including executed driving maneuvers, that is processed by the risk detection module 114 in an appropriate manner to determine whether or not a vehicle operator is exhibiting high risk driving, which may occur at specified time intervals or upon exceeding a risk threshold. Data provided by the plurality of sensors 106 is analyzed and compared to pre-defined threshold criteria, which may include a default risk threshold within the system or may include a risk threshold configured by a responsible party for a vehicle 100.

The notification module 116 receives information from the other modules (104, 110, 112, 114) in the operator impairment detection and reporting system 102 and reports the information to a responsible party of the vehicle 100. In certain embodiments, the report or notification is sent to the responsible party of the vehicle 100 in the form of an electronic communication, such as a courtesy telephone call, a text message, or an email. In some embodiments, the report is retrievable from the display portion of the user interface 108 of the vehicle 100 or from a webpage on the internet. In other embodiments, the report is retrievable from the display portion of a user interface of another vehicle, where both vehicles share a common owner and/or responsible party.

In one embodiment, the notification module 116 includes or cooperates with an onboard vehicle communication or telematics system, such as an OnStar® module commercially marketed and sold by the OnStar® corporation, which is a subsidiary of the assignee of the instant Application, the General Motors Company, currently headquartered in Detroit, Mich. In embodiments wherein the notification module 116 is an OnStar® module, an internal transceiver may be capable of providing bi-directional mobile phone voice and data communication, implemented as Code Division Multiple Access (CDMA). In some embodiments, other 3G technologies may be used to implement the notification module 116, including without limitation: Universal Mobile Telecommunications System (UMTS) wideband CDMA (W-CDMA), Enhanced Data Rates for GSM Evolution (EDGE), Evolved EDGE, High Speed Packet Access (HSPA), CDMA2000, and the like. In some embodiments, 4G technologies may be used to implement the notification module, alone or in combination with 3G technologies, including without limitation: Evolved High Speed Packet Access (HSPA+), Long Term Evolution (LTE) and/or Long Term Evolution-Advanced (LTE-A).

In certain embodiments, the notification module 116 may communicate reports using any network permitting data communication including, but not limited to, cellular networks, satellite networks, open content delivery networks, the Internet, or any other digital networks based upon TCP/IP or other conventional protocols, as well as combinations thereof. The notification module 116 may also utilize a wide area network (WAN), a local area network (LAN), or a combination thereof conforming to, for example, IEEE 802.3 and/or IEEE 802.11 standards and implemented within the vicinity of the location of the vehicle 100 such that notification module 116 may join the network when the vehicle 100 is parked and/or located within the general vicinity of the network.

Figure 2:
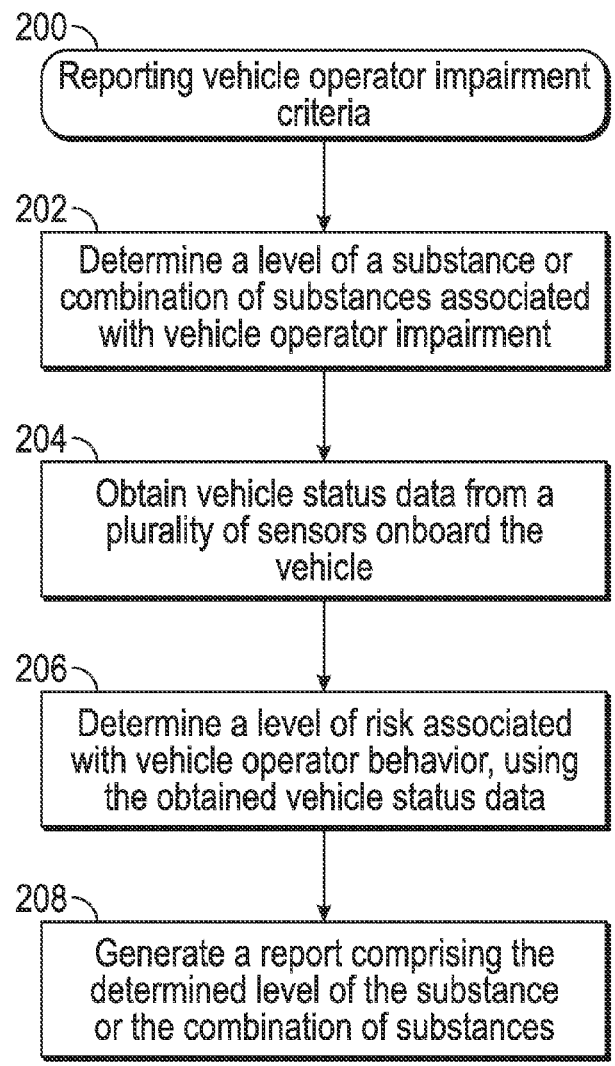
FIG. 2 is a flow chart that illustrates an embodiment of reporting vehicle operator impairment criteria.

FIG. 2 is a flow chart that illustrates an embodiment of a process 200 of reporting operator impairment criteria. The various tasks performed in connection with a process described here may be performed by software, hardware, firmware, or any combination thereof. For illustrative purposes, the description of a process may refer to elements mentioned above in connection with FIG. 1. In practice, portions of a described process may be performed by different elements of the described system, e.g., the control module, the user interface, the identification module, the substance detection module, the risk detection module, the notification module, or other components of the system. It should be appreciated that a described process may include any number of additional or alternative tasks, the tasks shown in the figures need not be performed in the illustrated order, and that a described process may be incorporated into a more comprehensive procedure or process having additional functionality not described in detail herein. Moreover, one or more of the tasks shown in the figures could be omitted from embodiments of a described process as long as the intended overall functionality remains intact.

For ease of description and clarity, this example assumes that the process 200 begins when a module or subsystem onboard the vehicle determines a level of a substance or combination of substances associated with vehicle operator impairment (step 202). In certain embodiments, the substance may be alcohol, any designated or listed type of drug (prescription, over the counter, illegal, etc.), a designated or listed chemical or compound, or the like. A "combination of substances" will typically be a defined combination of at least two different substances, wherein the different substances are determined to be present at or near the same time. For the example presented here, the onboard system monitors for the combination of alcohol and one or more designated drugs. Generally, the substance or combination of substances includes anything which may impair the ability of a person to operate a vehicle. In some embodiments, the process 200 may detect a level of a substance or combination of substances equal to zero, indicating a lack of presence of a substance associated with vehicle operator impairment.

Next, the process 200 obtains vehicle status data from a plurality of sensors onboard the vehicle (step 204). In some embodiments, the process 200 polls the plurality of sensors to obtain data, and in certain embodiments, this polling occurs on a timed loop. The plurality of sensors may collect data from the time the ignition is turned on until the ignition is turned off, and the data may include a number and/or time duration of specific driving maneuvers. These driving maneuvers may include maneuvers labeled "high risk", such as high g accelerations, high g decelerations, high speeds, high lateral acceleration readings, and the like. Other high risk driving maneuvers may be detected by the plurality of sensors, either alone or in combination with the previously described list of high risk maneuvers.

After obtaining vehicle status data from the plurality of sensors (step 204), the process 200 determines a level of risk associated with vehicle operator behavior, using the obtained vehicle status data (step 206). The determined level of risk indicates whether or not the associated vehicle operator behavior falls into the category of "high risk". The level of risk is determined using factors such as the number and duration of high risk driving maneuvers performed within a specified time period. In some embodiments, this specified time period may be a default value existing in the system, and in other embodiments, this specified time period may be configured by an owner or responsible party for the vehicle. In addition, the number and time duration thresholds may include default values which may be altered by a responsible party of the vehicle.

Next, the process 200 generates a report comprising the determined level of the substance or combination of substances (step 208). This notification is based on predetermined reporting rules which dictate that notification must be given to an owner and/or responsible party of a vehicle in certain situations. In some embodiments, these predetermined reporting rules include default parameters that have been programmed into the system at the design level, and in other embodiments, the predetermined reporting rules include parameters which may be configurable by a responsible party for a vehicle.

The predetermined rules include parameters for reporting vehicle operating behaviors to an owner and/or responsible party of a vehicle. For example, these parameters include minimum thresholds for levels of alcohol, drugs, and high risk vehicle operating behavior. Each threshold is adjustable, and varies based on substance type, driver identification, and vehicle type. The urgency of the report notification (e.g., immediate, delayed, retrieved by the user on demand, scheduled, or periodic) and the method of the report (e.g., courtesy call, text message, email, etc.) varies based on the extent of the measured level above the pre-defined, owner-configurable threshold. For example, for a 17 year old driver, who is not the owner or responsible party of the vehicle, normal reporting procedures are used when detecting a range of Blood Alcohol Content (BAC) of 0.02% to 0.05%, but when detecting a range of BAC above 0.05% an urgent text message is sent to a responsible party of the vehicle. In another example, for a 21 year old driver who is not a responsible party of the vehicle, normal reporting procedures are used when detecting BAC above 0.05%, but an urgent text message is sent to a responsible party of the vehicle when a detected BAC is over 0.07%.

Figure 3:
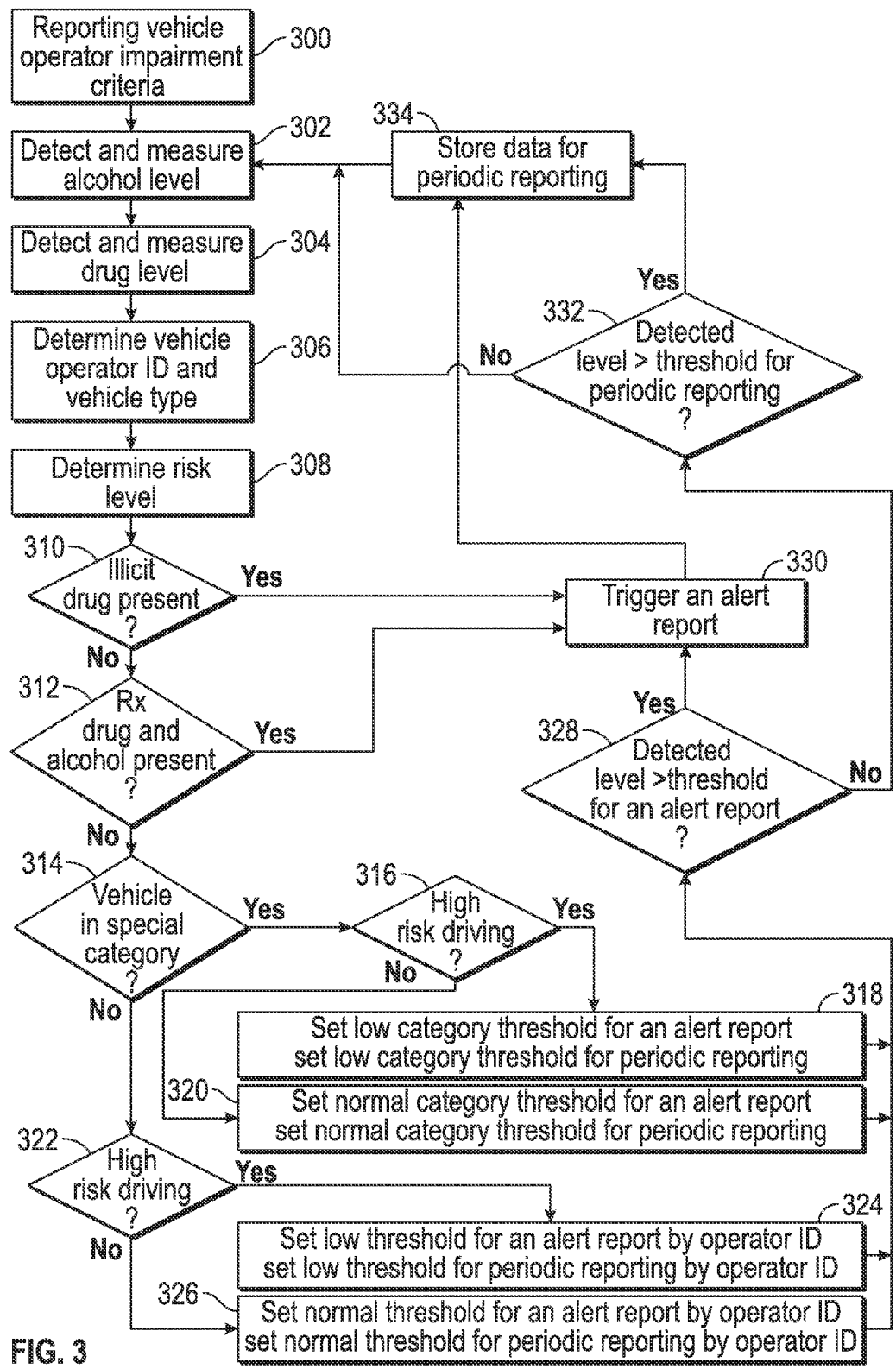
FIG. 3 is a flow chart that illustrates another embodiment of reporting vehicle operator impairment criteria.

FIG. 3 is a flow chart that illustrates another, more detailed, embodiment of a process 300 of reporting operator impairment criteria. For ease of description and clarity, this example assumes that the process 300 begins when an onboard module or subsystem detects and measures a level of alcohol in a vehicle (step 302). In some situations, the detected level of alcohol may be zero; nonetheless, the "zero" level is still recorded. Thereafter, the process 300 will store the data associated with the measured level of alcohol for further use and analysis, and continue to the next step.

Next, the process 300 detects and measures a level of one or more drugs in a vehicle (step 304). In some embodiments, the one or more drugs may include illegal drugs, prescription drugs, and/or any substance which may impair the ability of a person to operate a vehicle. The step of detecting and measuring a level of one or more drugs in the vehicle (step 304) occurs under all circumstances, and is not changed or otherwise affected by any detection (or lack of detection) of the presence of alcohol in the vehicle. At the completion of step 304, the process 300 may record data that indicates the presence (or lack thereof) of any number of monitored drugs and, if any of those drugs are present, the respective level or amount of the drugs present.

The process 300 then determines the identification of a vehicle operator and a vehicle type (step 306). In some embodiments, the identification may simply indicate whether or not the current operator of the vehicle is also the owner and/or responsible party of the vehicle. In this example, the same default and/or owner-configurable thresholds and reporting rules may be applied to all non-owners or non-responsible parties. In addition, a commonly used, default and/or owner-configurable set of thresholds and reporting rules for one or more owners or responsible parties may be distinguished from those assigned to non-owners or non-responsible parties. In this example, each specific category or group of vehicle operators (i.e., owners versus non-owners) has been assigned a common set of reporting rules within the system. In certain embodiments, this is to ensure that more stringent reporting rules may be applied to a non-owner when operating a vehicle. In some embodiments, the identity of the vehicle operator may include a specific identity of an individual, and in this example, an individual may be assigned driver-specific reporting rules within the system.

Generally, when a vehicle is designated as assigned to a particular group of vehicle operators, particular parameters and reporting rules may be assigned to the vehicle itself, such as reporting threshold values for measured levels of alcohol and/or one or more drugs, or reporting threshold values including vehicle operating behavior. In certain embodiments, the vehicle type includes a special category of vehicle that is assigned to a particular group of vehicle operators, including without limitation, a teen vehicle, a valet vehicle, a fleet vehicle, a rental vehicle, etc. Teen vehicles may include those vehicles designated by a responsible party as being operated primarily by one or more young drivers. A responsible party may configure a teen vehicle with specific thresholds for acceptable substance levels and/or risk levels that may be lower than those threshold levels that are appropriate for an older, more experienced driver. In this example, a responsible party, such as a parent, may configure a teen vehicle with thresholds appropriate for a vehicle operator who is under the legal age for drinking alcohol, or thresholds appropriate for a teen suspected of consuming recreational drugs. Additionally, responsible party may configure a teen vehicle with specific thresholds for acceptable risk levels appropriate for a younger vehicle operator. Furthermore, a vehicle which otherwise does not have a teen designation may still identify specific operators as teen operators, with their own reporting thresholds and criteria, based on the key or key fob used to operate the vehicle.

Valet vehicles may include those vehicles designated by a responsible party as being operated often by a valet or parking attendant. A responsible party may configure a valet vehicle with specific thresholds for acceptable substance levels and/or risk levels that reflect acceptable behavior for a valet or parking attendant. In this example, a responsible party may prefer that a valet or parking attendant driving his/her vehicle not consume any alcohol or drugs, or participate in any risky behavior while operating the vehicle. Furthermore, a vehicle which otherwise does not have a valet designation may still identify specific operators as valet operators, with their own reporting thresholds and criteria, based on the key used to operate the vehicle or upon a specific valet mode entered by the owner or responsible party prior to conveyance of the vehicle to the valet operator.

Fleet vehicles may include those vehicles designated by a responsible party as being operated primarily by a plurality of professionally employed vehicle operators, such as taxis, limousines, school buses, ambulances, police cars, construction vehicles, and the like. Additionally, fleet vehicles may include boats, trains, and airplanes. In all of these cases, specific thresholds for acceptable substance levels and/or risk levels may be set for a fleet of vehicles, by a responsible party, such as a fleet supervisor. For example, an acceptable substance level for a school bus driver or an ambulance driver may be set to zero, or whatever threshold level deemed appropriate by a responsible party for the fleet.

Rental vehicles may include those vehicles designated by a responsible party as being operated primarily by paying customers for a temporary period of time before being returned, such as cars, trucks, sport utility vehicles, or recreational vehicles, such as snowmobiles, all-terrain vehicles, and jet skis. A responsible party, such as an owner, may configure his/her rental vehicles with specific thresholds for acceptable substance levels and/or risk levels. For example, an acceptable substance level for a rental jet ski may be set to a Blood Alcohol Content (BAC) of 0.02%, possibly allowing for a drink or two on the part of the vehicle operator, which is well under the legal limit for vehicle operation.

The step of determining the identification of a vehicle operator and a vehicle type (step 306) results in the process 300 accessing or consulting a specific group of thresholds, which are dictated by the vehicle operator identification and the vehicle type. Once the process 300 has accessed this specific group of thresholds, these thresholds may be applied as needed to support the remaining steps in the process 300.

Next, the process 300 determines a risk level (step 308), based on maneuvers executed during vehicle operation. An acceptable threshold for the risk level is an owner-configurable parameter, and reporting rules governing what constitutes high risk behavior will depend upon owner or responsible party preference. An appropriate threshold for high risk behavior is configured by the owner or responsible party, utilizing a number of occurrences within a specified time period and/or time duration of high risk maneuvers. For example, an owner may configure the system to dictate that two lateral g accelerations in a ten minute period for a fleet vehicle indicates high risk behavior, or that speeds above 80 miles per hour for a period of ten minutes indicates high risk behavior. In another example, an owner may configure the system to dictate that any type of "panic" braking (i.e., braking hard) in a teen vehicle indicates high risk behavior. For this particular implementation, step 308 results in a determination of whether or not high risk driving has been detected.

The process 300 then proceeds to determine if an illicit drug is present (step 310). In certain embodiments, an illicit drug includes an illegal controlled substance which may or may not have a legitimate medical use and which has the capability to impair the ability of a person to operate a vehicle. In some embodiments, an illicit drug may include a legal controlled substance, such as a legal recreational drug which has the capability to impair the ability of a person to operate a vehicle.

When the presence of an illicit drug has been confirmed (the "Yes" branch of 310), the process 300 triggers an alert report of the information (step 330) to a responsible party of the vehicle. This alert report may include a courtesy telephone call, a text message, an email, or a report appearing on a vehicle display. In some embodiments, an alert report is issued immediately (or within a reasonably short period of time, such as one minute, five minutes, or the like), once the alert report has been triggered. In practice, an alert report can be triggered once a threshold level of the substance has been exceeded, or an alert report can be triggered merely upon detection of the presence of a specific substance or combination of substances.

Following the alert report of the information (step 330), the process 300 also stores the data for periodic reporting (step 334), and then returns to the beginning of the process (step 302). In certain embodiments, periodic reporting may include a report issued to a responsible party of the vehicle at specified time intervals. For example, periodic reporting may include a generated monthly report that is transmitted electronically (e.g., via email), via conventional delivery methods (e.g., via postal mail), and/or transmitted to a vehicle display within the vehicle itself, or another designated vehicle.

When the presence of an illicit drug has not been confirmed (the "No" branch of 310), the process 300 proceeds to determine if a prescription (or any designated type) drug, in combination with alcohol, is present (step 312). When the presence of a prescription drug in combination with alcohol is present (the "Yes" branch of 312), the process 300 triggers an alert report of the information (step 330). As described previously, this alert report (step 330) leads to storing the data for periodic reporting (step 334), and then returning to the beginning of the process (step 302).

When the presence of a prescription drug in combination with alcohol is not present (the "No" branch of 312), the process 300 proceeds to determine if the vehicle type is within a special category (step 314).

When the vehicle has been determined to be in a special category (the "Yes" branch of 314), and is determined to be conducting high risk driving maneuvers (the "Yes" branch of 316), the process 300 will set low thresholds, based on the special category of the vehicle, for both alert and periodic reporting (step 318). For example, if a teen vehicle is determined to be conducting high risk driving maneuvers, the process 300 will set low reporting thresholds, so that the owner of the teen vehicle will be notified when a relatively small amount of high risk behavior is exhibited by an operator of the teen vehicle. In this example, an owner or responsible party is notified before the risk has the opportunity to escalate.

When the vehicle has been determined to be in a special category (the "Yes" branch of 314), and is determined not to be conducting high risk driving maneuvers (the "No" branch of 316), the process 300 will set normal thresholds, based on the special category of the vehicle, for both alert and periodic reporting (step 320). For example, if a fleet vehicle is determined not to be conducting high risk driving maneuvers, the process 300 will set normal reporting thresholds, so that a responsible party of the fleet vehicle will be notified when a normal amount of high risk behavior is exhibited by an operator of the fleet vehicle. In this example, a normal amount of high risk behavior is a parameter that is configurable by a responsible party of the vehicle. In certain embodiments, a normal threshold may be set at 25% above a $50^{th}$ percentile of an average range of daily driving behavior, when the average range is calculated for each driving maneuver over a specified period of time.

When the vehicle has been determined not to be in a special category (the "No" branch of 314), and is determined to be conducting high risk driving maneuvers (the "Yes" branch of 322), the process 300 will set low thresholds, based on the identity of the vehicle operator, for both alert and periodic reporting (step 324). In certain embodiments, pre-defined thresholds are stored within the system and retrieved and applied to specific circumstances when necessary. In some embodiments, a low reporting threshold for a measured level of alcohol for a particular driver would not be considered a low reporting threshold for a measured level of alcohol for another driver. For example, the process 300 may set a normal reporting threshold of 0.08% Blood Alcohol Content (BAC) for a valet vehicle, because this particular value of BAC would result in arrest for a vehicle operator in any location in the United States. A low reporting threshold, in this example, would be 0.04% BAC, and this low reporting threshold may be deemed necessary by a responsible party of the vehicle when high risk behavior is exhibited by a valet vehicle operator. In another example, the process 300 may set a normal reporting threshold of 0.01% BAC for a teen vehicle, and the "low" reporting threshold of 0.04% set for a valet vehicle, in this case, would not be considered a low reporting threshold for the teen vehicle.

If the vehicle has been determined not to be in a special category (the "No" branch of 314), and is determined not to be conducting high risk driving maneuvers (the "No" branch of 322), the process 300 will set normal thresholds, based on the identity of the vehicle operator, for both alert and periodic reporting (step 326). For example, an owner and spouse of the owner may be identified as individuals within an operator impairment detection and reporting system, and when either the owner or the spouse are determined to be driving normally (i.e., not conducting high risk driving maneuvers), the process 300 will set normal reporting thresholds for each, based on pre-defined, owner-configurable parameters. In this example, the owner may have set his/her own normal threshold for BAC as 0.08%, but the owner may have set a normal BAC reporting threshold for his/her spouse of 0.02%.

After setting the applicable reporting thresholds (steps 318, 320, 324, 326), the process 300 determines whether a detected level is greater than the threshold that has been set for an alert report (step 328). The detected level indicates the previously detected and measured levels of alcohol and/or one or more drugs, and the process 300 compares these levels to the pre-defined thresholds that have been selected by the process 300 based on exhibited high risk behavior or lack thereof.

When the detected level has been determined to be greater than the threshold for an alert report (the "Yes" branch of 328), the process 300 triggers an alert report (step 330), followed by storing the applicable data for periodic reporting (step 334) and returning to the beginning of the process (step 302). When the detected level has been determined not to be greater than the threshold for an alert report (the "No" branch of 328), the process 300 proceeds to determine if the detected level is greater than the threshold that has been set for periodic reporting (step 332). If so (the "Yes" branch of 332), then the process 300 stores the data for periodic reporting (step 334), and then returns to the beginning of the process (step 302). If not (the "No" branch of 332), then the process 300 returns to the beginning of the process (step 302).

In certain embodiments, periodic reporting in the system may include a report that is generated at time intervals, such as a weekly or monthly report. In some embodiments, the report is appended to an already-generated monthly email report for OnStar®, which details various parameters related to operation of a vehicle. In some embodiments, the weekly or monthly report is delivered to a responsible party of the vehicle via mailed or faxed hardcopy, email report, reported data sent via text message, and/or vehicle display report.

The data that is included in the periodic reporting (step 334) includes all data applicable for an alert report (step 330) and periodic reporting. All data meeting the criteria for an alert report is stored for periodic reporting. In addition, due to owner-configurable parameters and thresholds, an owner may configure the system to report all data, an owner-selected subset of data, or no data at all. Generally, data included in an alert report includes an indication that a pre-defined, owner-configurable threshold has been exceeded, and this particular threshold has been selected by the owner as requiring immediate attention when exceeded. In certain embodiments, an alert report only includes a measured level of one or more impairing substances present in the vehicle, in which the measured level exceeds a pre-defined threshold.

In some embodiments, data included in a periodic report may include, without limitation: average substance level, peak substance level, number of times a pre-defined threshold exceeded, number of times vehicle start and/or vehicle usage is inhibited, number of times any substance is detected, operation of any system overrides/backup mechanisms which may be present, and/or detailed reporting of any detected high risk driving maneuvers. The average and peak substance levels may be calculated over a specified period of time. Generally, the average substance level may be represented by a mean, median, or mode, of all detected substance levels over a period of time, according to designer preference and/or owner-configuration. The peak substance value may be represented by the highest detected level of a substance over a period of time configured by an owner or responsible party of the vehicle. In some embodiments, the average and peak substance levels may include data regarding a presence and/or level of a combination of substances. In certain embodiments, an owner or responsible party may configure the average and peak substance levels to be calculated on a monthly basis, to be included in a monthly periodic report. In some embodiments, the average and peak substance levels may be calculated on a weekly basis, or another period of time configured by a responsible party, and reported on a periodic report generated according to any specified time interval.

The number of times a pre-defined threshold is exceeded may be calculated over a specified period of time, which may be configured by a responsible party of the vehicle. The pre-defined threshold may be any substance level or risk level threshold relevant or applicable to the process of reporting vehicle operator impairment (shown in FIGS. 2-3). In certain embodiments, a responsible party may configure the number of times a pre-defined threshold is exceeded to be calculated on a weekly or monthly basis, to be included in a periodic report generated according to any specified time interval.

The number of times vehicle start and/or vehicle usage is inhibited may also be calculated over a specified period of time, which may be configured by a responsible party of the vehicle. In certain embodiments, this may be performed in addition to either a voluntary or court-ordered installation of a vehicle/ignition interlock system which immobilizes the vehicle for certain (or any) operators based upon detection of specific substances. For example, a vehicle could be equipped with a breathalyzer based alcohol detection system which requires the sampling of breath alcohol content before allowing the starting event on every driver cycle. For such a vehicle installation, the number of starting events for which starting is authorized, as well as those events for which starting is inhibited, may be counted in aggregate or over the period of time between reporting events.

The number of times any substance is detected may be calculated over a specified period of time, and generally indicates any time the detected level of a substance is greater than zero. In certain embodiments, a responsible party may configure the number of times any substance is detected to be calculated on a weekly or monthly basis, to be included in a periodic report generated according to any specified time interval.

The operation of any system overrides/backup mechanisms which may be present indicates anytime a vehicle operator disables the vehicle operator impairment reporting mechanism, or creates a condition in which the vehicle operator behavior or impairment will not be reported. The operation of any system overrides/backup mechanisms may be counted numerically over a period of time, to be included in a periodic report generated according to any specified time interval.

Detailed reporting of any detected high risk driving maneuvers may include a numerical count and/or time duration of any detected high risk driving maneuvers, along with additional data collected by various sensors in the vehicle. Generally, over a specified period of time, high risk driving maneuvers are identified, counted, timed, and attributed to an identified vehicle operator. In certain embodiments, all of this data is included in a periodic report, generated according to any specified time interval. In some embodiments, only a portion of the data is included in the periodic report, as configured by a responsible party of the vehicle.

Techniques and technologies may be described herein in terms of functional and/or logical block components, and with reference to symbolic representations of operations, processing tasks, and functions that may be performed by various computing components or devices. Such operations, tasks, and functions are sometimes referred to as being computer-executed, computerized, software-implemented, or computer-implemented. In practice, one or more processor devices can carry out the described operations, tasks, and functions by manipulating electrical signals representing data bits at memory locations in the system memory, as well as other processing of signals. The memory locations where data bits are maintained are physical locations that have particular electrical, magnetic, optical, or organic properties corresponding to the data bits. It should be appreciated that the various block components shown in the figures may be realized by any number of hardware, software, and/or firmware components configured to perform the specified functions. For example, an embodiment of a system or a component may employ various integrated circuit components, e.g., memory elements, digital signal processing elements, logic elements, look-up tables, or the like, which may carry out a variety of functions under the control of one or more microprocessors or other control devices.

While at least one exemplary embodiment has been presented in the foregoing detailed description, it should be appreciated that a vast number of variations exist. It should also be appreciated that the exemplary embodiment or embodiments described herein are not intended to limit the scope, applicability, or configuration of the claimed subject matter in any way. Rather, the foregoing detailed description will provide those skilled in the art with a convenient road map for implementing the described embodiment or embodiments. It should be understood that various changes can be made in the function and arrangement of elements without departing from the scope defined by the claims, which includes known equivalents and foreseeable equivalents at the time of filing this patent application.

What is claimed is:

1. A method for reporting vehicle operator impairment criteria, comprising:
   determining, using a substance detection device installed inside a vehicle, a level of a substance or combination of substances associated with vehicle operator impairment;
   obtaining vehicle status data from a plurality of sensors onboard the vehicle, wherein the vehicle status data comprises a quantity of driving maneuvers and a duration of the driving maneuvers, and wherein the driving maneuvers were executed within a specified time period;
   determining a level of risk associated with vehicle operator behavior, using the obtained vehicle status data, by:
      identifying the quantity and duration of the driving maneuvers; and
      comparing the quantity and duration of the driving maneuvers to predetermined threshold data to determine a high level of risk or a low level of risk; and
   generating a report, comprising the determined level of the substance or the combination of substances and the determined level of risk.

2. The method for reporting of claim 1, further comprising:
   determining an identification of a driver of the vehicle, and based on the identification of the driver of the vehicle:
      setting a driver-specific threshold level of the substance or the combination of substances for alert reporting; and
      setting a driver-specific threshold level of the substance or the combination of substances for periodic reporting.

3. The method of reporting of claim 2, wherein the determining the identification of the driver of the vehicle comprises analyzing a unique ignition key used to operate the vehicle.

4. The method for reporting of claim 1, wherein the generated report comprises a transmitted electronic communication from the communication device.

5. The method for reporting of claim 1, further comprising, for a designated period of time:
   calculating an average level of the substance or the combination of substances; and
   communicating the calculated average level of the substance or the combination of substances to the communication device to generate the report;
   wherein the report comprises the calculated average level of the substance or the combination of substances.

6. The method for reporting of claim 1, further comprising, for a designated period of time:
   calculating a peak level of the substance or the combination of substances; and
   communicating the calculated peak level of the substance or the combination of substances to the communication device to generate the report;
   wherein the report comprises the calculated peak level of the substance or the combination of substances.

7. The method for reporting of Claim 1, further comprising, for a designated period of time:
   determining a number of occurrences in which a reading level for the substance or the combination of substances exceeds a threshold level; and communicating the determined number of occurrences to the communication device to generate the report;
wherein the report comprises the determined number of occurrences.

8. The method for reporting of claim 1, further comprising, for a designated period of time:
determining a number of occurrences in which the substance or the combination of substances is detected; and
communicating the determined number of occurrences to the communication device to generate the report;
wherein the report comprises the determined number of occurrences.

9. The method for reporting of claim 1, further comprising, for a designated period of time:
determining a number of system override activations; and
communicating the determined number of system override activations to the communication device to generate the report;
wherein the report comprises the determined number of occurrences.

10. A system for reporting impaired operation of a vehicle, the system comprising:
a substance detection module, configured to examine a driver for presence of a substance that is likely to cause impaired driving;
a risk detection module, configured to determine a risk level associated with a current operation of the vehicle by the driver, by:
identifying a quantity and a duration of one or more driving maneuvers executed within a specified time period; and
comparing the quantity and the duration of the driving maneuvers to predetermined threshold data to determine a high level of risk or a low level of risk; and
a notification module, configured to:
trigger an alert notification when:
the substance detection module detects presence of the substance at a level exceeding an alert notification substance threshold; and
the risk detection module determines a risk level exceeding an alert notification risk threshold.

11. The system of claim 10, further comprising:
an identification module, configured to identify a driver and a designation of the vehicle;
wherein the alert notification substance threshold is calculated as a function of the determined risk level and the identification of the driver.

12. The system of claim 10, wherein the alert notification substance threshold is further calculated as a function of the determined risk level and the identified designation of the vehicle.

13. The system of claim 10, wherein the alert notification comprises an electronic communication transmitted by the notification module upon exceeding the alert notification substance threshold or the alert notification risk threshold.

14. The system of claim 11, wherein the notification module is further configured to:
trigger periodic notification when the substance detection module detects presence of the substance at a level exceeding a periodic notification substance threshold; and
trigger periodic notification when the risk detection module determines a risk level exceeding a periodic notification risk threshold.

15. The system of claim 14, wherein the periodic notification comprises an email report generated and sent, at regular time intervals, to a responsible party of the vehicle.

16. The system of claim 14, wherein, when the identification module identifies a driver that is not a responsible party of the vehicle and a designation of the vehicle that indicates a special category vehicle, the notification module is further configured to:
trigger an alert notification when the substance detection module detects a level of the substance exceeding a second alert notification substance threshold;
trigger an alert notification when the risk detection module determines a risk level exceeding a second alert notification risk threshold;
trigger periodic notification when the substance detection module detects a level of the substance exceeding a second periodic notification substance threshold; and
trigger periodic notification when the risk detection module determines a risk level exceeding a second periodic notification risk threshold.

17. A system for determining timing and priority of notification of impaired driving, the system comprising:
a processor architecture;
a memory, communicatively coupled to the processor architecture, wherein the memory is configured to store received data and instructions executable by the processor architecture;
a plurality of sensors, communicatively coupled to the processor architecture, and configured to collect data associated with operation of a vehicle, wherein the data comprises a quantity and a duration of driving maneuvers executed within a specified time period; and
an impairing substance detection unit, communicatively coupled to the processor architecture, and configured to test for a level of an impairing substance;
wherein the processor architecture is configured to:
determine a presence and a level of the impairing substance, using data received from the impairing substance detection unit;
detect impaired driving behavior using the data collected by the plurality of sensors;
determine a risk level based on the impaired driving behavior, by:
identifying the quantity and duration of the driving maneuvers; and
comparing the quantity and duration of the driving maneuvers to predetermined threshold data to determine a high level of risk or a low level of risk; and
initiate a report detailing the impaired driving behavior, the risk level, and the presence of an impairing substance.

18. The system of claim 17, wherein the initiated report further comprises:
an alert report when the level of the impairing substance exceeds an alert notification substance threshold; and
a periodic report when the level of the impairing substance exceeds a periodic notification substance threshold.

19. The system of Claim 17, wherein the initiated report comprises a notification within a generated monthly vehicle data report.

20. The system of claim 17, wherein the alert report comprises an electronic communication transmitted upon exceeding an alert report substance threshold or an alert report risk threshold.

* * * * *